United States Patent [19]
Odom

[11] Patent Number: 5,645,058
[45] Date of Patent: Jul. 8, 1997

[54] CAP WITH SUPPORT FOR MEDICAL TUBING

[76] Inventor: Donald M. Odom, 10215 W. Landmark Ct., Boise, Id. 83704

[21] Appl. No.: 548,287

[22] Filed: Oct. 25, 1995

[51] Int. Cl.⁶ ........................................ A62B 7/00
[52] U.S. Cl. ................. 128/207.18; 128/201.22; 128/DIG. 26
[58] Field of Search .......... 128/207.18, 201.22, 128/DIG. 26; D2/866–869; 604/94, 174, 179

[56] References Cited

U.S. PATENT DOCUMENTS

| | | | |
|---|---|---|---|
| 2,259,817 | 10/1941 | Hawkins | 128/DIG. 26 |
| 3,648,703 | 3/1972 | Manker | 128/DIG. 26 |
| 4,367,735 | 1/1983 | Dali | 128/203.22 |
| 4,406,283 | 9/1983 | Bir | 128/DIG. 26 |
| 4,641,647 | 2/1987 | Behan | 128/DIG. 26 |
| 4,665,566 | 5/1987 | Garrow | 2/171 |
| 4,739,757 | 4/1988 | Edwards | 128/DIG. 26 |
| 4,739,905 | 4/1988 | Nelson | D2/866 |
| 4,774,946 | 10/1988 | Ackerman et al. | 128/207.18 |
| 4,808,160 | 2/1989 | Timmons et al. | 128/DIG. 26 |
| 4,836,200 | 6/1989 | Clark | 128/DIG. 26 |
| 5,188,101 | 2/1993 | Tumolo | 128/207.18 |

*Primary Examiner*—Edgar S. Burr
*Assistant Examiner*—Daniel J. Colilla
*Attorney, Agent, or Firm*—Ken J. Pedersen; Barbara S. Pedersen

[57] ABSTRACT

This invention is a snug, soft cap for wearing on the head and for supporting nasal oxygen cannula or other medical tubing. The cap has a plurality of integral supports, preferably for placement above and behind the ears of the wearers. Preferably, the supports are vertically depending strips of fabric attached at their top, inside surface near the bottom edge of the cap, and having cooperating hook and loop patch fasteners at the top and bottom of their outside surface. This way, the strips may be closed outside bottom end to outside top end to make loops for receiving and securing the medical tubing. Also, the medical tubing may pass through closed loops on the cap, and thus be permanently or semi-permanently attached to the cap.

1 Claim, 3 Drawing Sheets

CAP WITH SUPPORT FOR MEDICAL TUBING

BACKGROUND OF THE INVENTION

1. Field of the Invention

This invention generally pertains to the medical care, and more specifically it pertains to a cap worn on a patient's head for supporting medical tubing to the head.

2. Description of Related Art

Several devices have been used to fasten and support medical tubing to the head. For example, U.S. Pat. No. 4,665,566 (Garrow) discloses an adjustable strap with hook and loop fasteners which may be closed around medical tubing for fastening and supporting the tubing to an extremity. In one embodiment of the invention, the strap is the headband of the hat with a shaped crown and a bill, brim or visor. Also, U.S. Pat. No. 5,188,101 (Tumolo) discloses an adjustable headband with integral tie fasteners for supporting medical tubing to the head.

Still, there is a need for a comfortable headpiece which may be worn to fasten and support medical tubing to the head, even while the patient is sleeping or confined to bed.

SUMMARY OF THE INVENTION

This invention is a snug, soft cap for wearing on the head and for supporting nasal oxygen cannula or other medical tubing. The cap has a plurality of integral supports, preferably for placement above and behind the ears of the wearers. Preferably, the supports are vertically depending strips of fabric attached at their top, inside surface near the bottom edge of the cap, and having cooperating hook and loop patch fasteners at the top and bottom of their outside surface. This way, the strips may be closed outside bottom end to outside top end to make loops for receiving and securing the medical tubing. Alternately, the supports may be closed loops attached to the cap, with the medical tubing permanently or semi-permanently passing through the loops.

DESCRIPTION OF THE PREFERRED EMBODIMENTS

Figure 1:
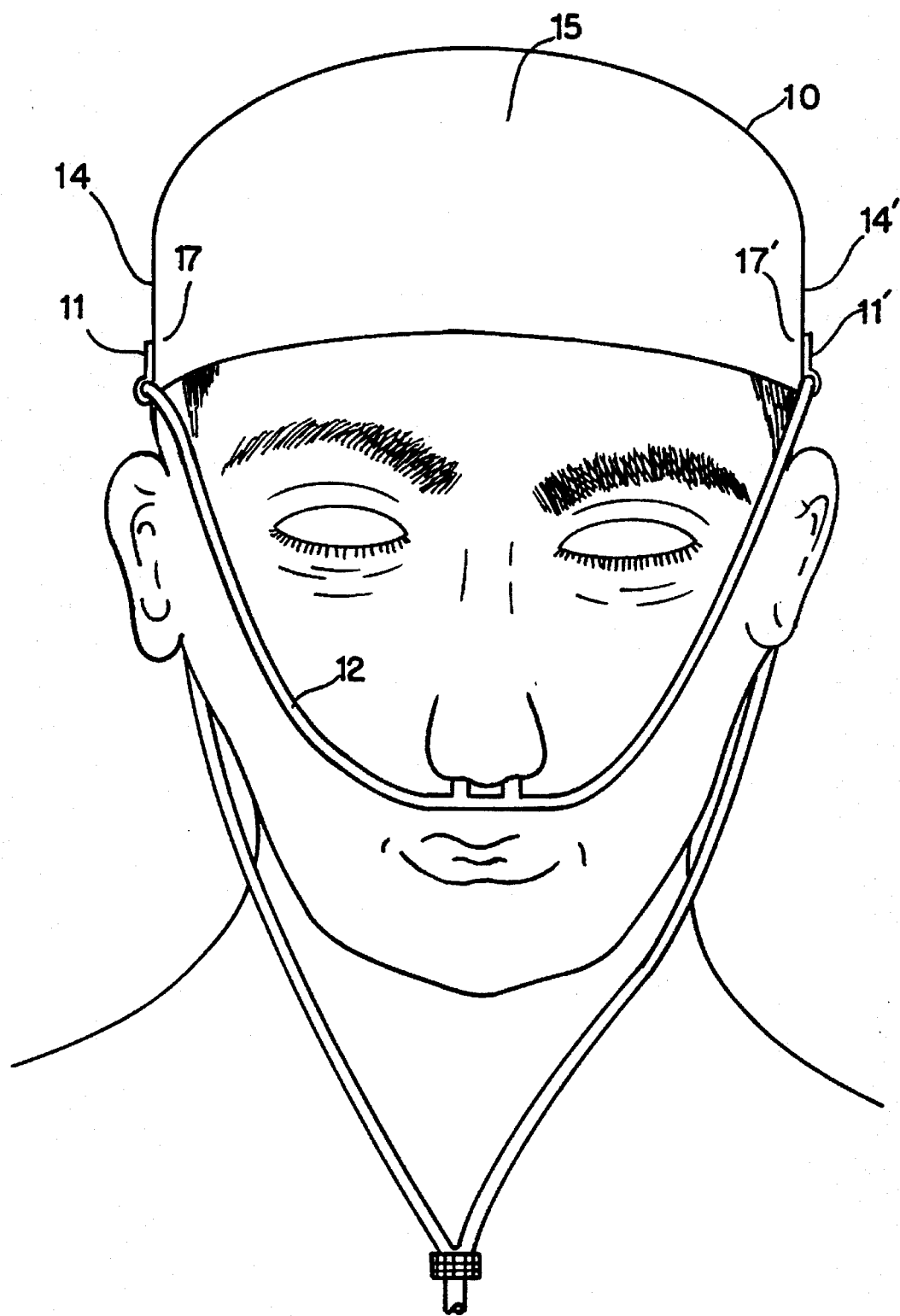
FIG. 1 is a front view of a person wearing an embodiment of the invention on the head.
Figure 2:
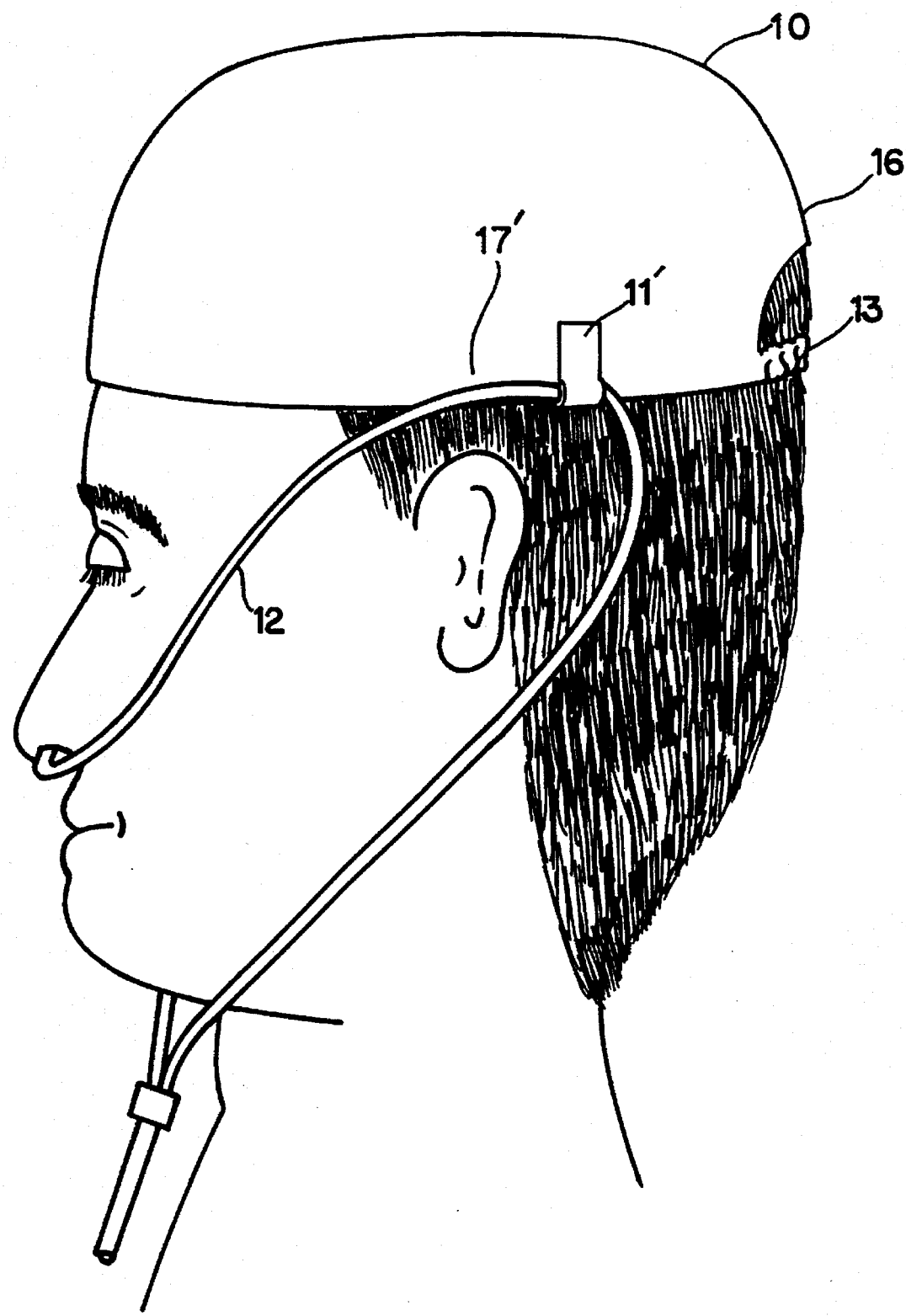
FIG. 2 is a left side view of the person in FIG. 1.
Figure 3:
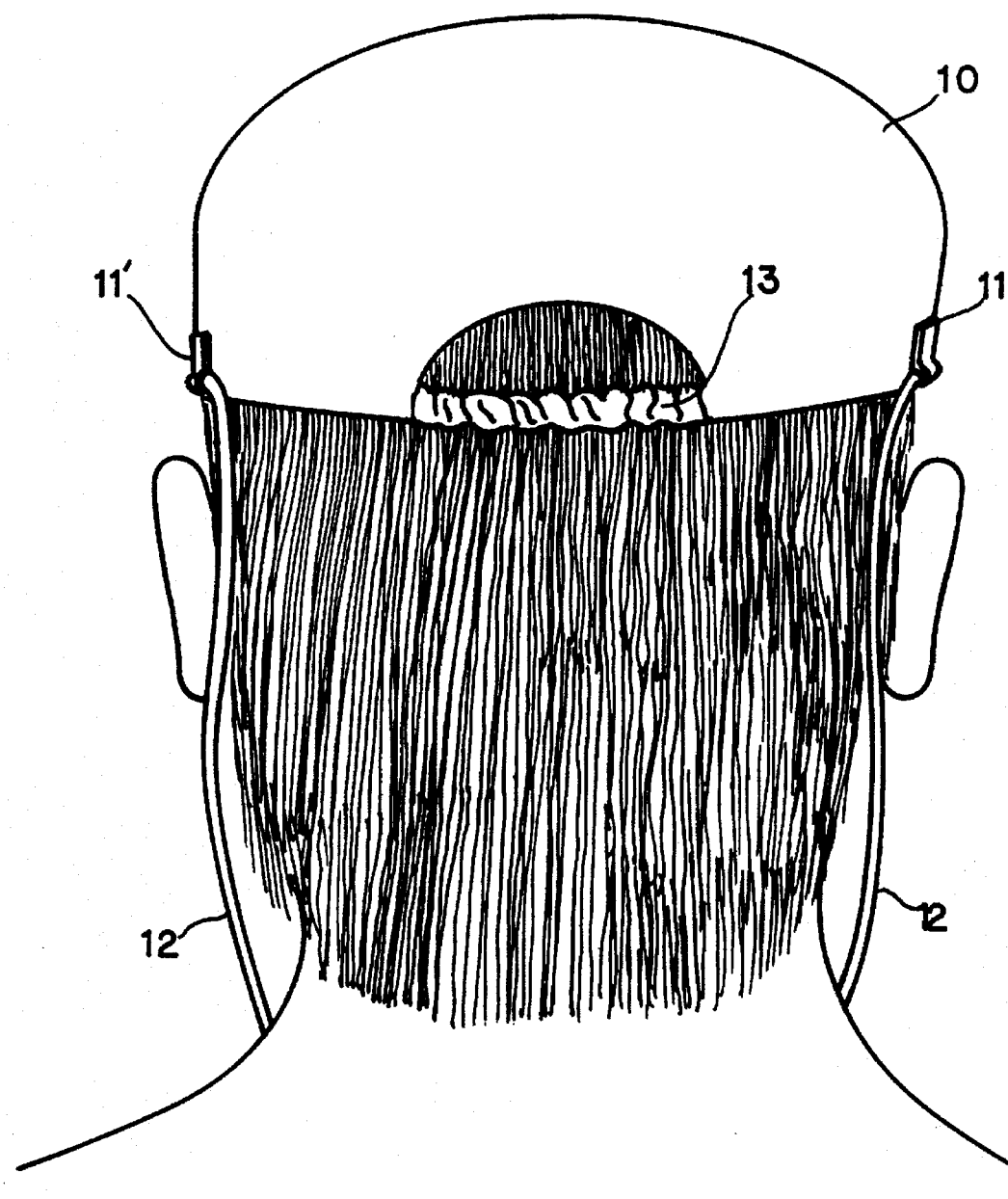
FIG. 3 is a rear view of the person in FIG. 1.

Referring to the Figures, there is depicted cap 10 with supports 11 and 11' positioned above and behind the ears for receiving and securing medical tubing 12 to the head of the wearer.

Medical tubing 12 extends from the front or face of the wearer up to and behind the ears, so that the tubing is fastened to the cap, which fits snugly on the head and does not contact the ears. Then, as shown in the Figures, tubing 12 extends from above and behind the ears to down beneath the chin in front of the neck and chest of the wearer. This way, the tubing 12 tends to rest on the chest of the wearer, where it is relatively safe from disturbance, and out of the way for comfort while the wearer is lying down or sleeping. Also, this way no part of the tubing is on the back of the head to get in the way and interfere with rest or sleep while the cap is in use.

Preferably, cap 10 has no shaped crown, and no brim. Also, preferably, cap 10 is made of a very soft material so that it may be snugly fitted to the head, one size of the cap 10 may fit most head sizes, and so that the cap is suitable for sleeping or bed confinement in that it will not be bulky or in the way or uncomfortable to lie on.

Preferably, the cap 10 covers a substantial portion of the top of the wearer's head, that is, a substantial portion of the parietal and frontal portions. Thus, the cap 10 stays securely in place by covering the top of the head instead of by having straps or ties that surround the head and that can rub or chafe the skin. Cap 10 may have an elastic portion 13 to help secure the cap to the head by taking up the slack in the fit.

Preferably, the cap 10 may be "breathing", air-permeable fabric or may have apertures or include loosely-woven fabric to allow air and moisture to pass through the cap 10.

Supports 11 and 11' may be any structure suitable near the lower edge of the cap for receiving and securing the medical tubing. Supports 11 and 11' may be clamps, loops, or ties or any suitable means for supporting medical tubing. Supports 11 and 11' are located on cap 10 so that they may be positioned above and behind the ears of the wearer. Also, supports 11 and 11' are integral with cap 10 in that they are securely attached to it and become part of it. Supports 11 and 11' are not part of a strap or band as in the Garrow patent. Preferably, supports 11 and 11' are vertically depending strips of fabric attached at their top inside surface near the bottom edge of the cap, and have cooperating hook and loop patch fasteners at the top and bottom of their outside surface. This way, the strips may be closed by connecting the outside bottom end patches to the outside top end patches to make loops for receiving and securing the medical tubing.

Preferably, the supports 11, 11' are on the cap sides 14, 14' at least half way back from the front 15 of the cap 10 towards the back 16 of the cap 10. In other words, the supports 11, 11' are preferably slightly behind the midpoints 17, 17' of the cap sides 14, 14', which typically corresponds to a position on the head slightly behind the ears and above the ears. Thus, when the tubing 12 rests in the supports 11, 11', it rests slightly behind and above the ears.

Tubing 12 may be any medical tubing, including tubing for nasal oxygen cannulas, nasal gastric tubes and intravenous tubes. Also, tubing 12 may also be electrical or other monitoring lines. An important feature of my invention is that the tubing 12 does not extend across the back of the head or neck during use of the cap. Instead, it extends down from above and behind the ears and forward to beneath and in front of the neck and on the chest.

Although this invention has been described above with reference to particular means, materials and embodiments, it is to be understood that the invention is not limited to these disclosed particulars, but extends instead to all equivalents within the scope of the following claims.

I claim:

1. A cap including means for supporting medical tubing on a wearer of the cap, said cap having a front, a back, and two sides having midpoints half-way between the said front and back, said cap being snugly fitted to a wearer's head, covering a substantial portion of the top of a wearer's head, not contacting the ears of a wearer, having said cap having no shaped crown and no brim, said means for supporting medical tubing including a plurality of integral supports, one on each side near the bottom edge of the cap and behind the midpoint of the side for receiving and supporting the medical tubing, said integral supports not being part of a strap or band of said cap, and said integral supports being located on the cap so they are positioned above and behind the ears of a wearer.

* * * * *